United States Patent [19]
Hatschek et al.

[11] Patent Number: 5,507,936
[45] Date of Patent: Apr. 16, 1996

[54] MEMBER FOR THE FORMATION OF AT LEAST ONE ELECTRODE AND/OR ONE SENSOR

[75] Inventors: Rudolf A. Hatschek, Friburg; Erich W. F. Heitz, Schaffhausen, both of Switzerland

[73] Assignee: AVL Medical Instruments AG, Schaffhausen, Switzerland

[21] Appl. No.: 421,278

[22] Filed: Apr. 13, 1995

Related U.S. Application Data

[63] Continuation of Ser. No. 73,444, Jun. 8, 1993, abandoned.

[30] Foreign Application Priority Data

Jun. 9, 1992 [CH] Switzerland ................. 1830/92

[51] Int. Cl.⁶ ................................................. G01N 27/414
[52] U.S. Cl. ..................... 204/412; 204/419; 204/433; 204/435; 205/777.5; 205/787.5; 205/789; 205/792
[58] Field of Search ........................... 204/153.21, 416, 204/419, 433, 412, 435

[56] References Cited

U.S. PATENT DOCUMENTS

| | | | |
|---|---|---|---|
| 2,928,775 | 3/1960 | Leisey | 204/405 |
| 3,726,777 | 4/1973 | Macur | 204/403 |
| 4,536,274 | 8/1985 | Papadakis et al. | 204/415 |
| 4,613,422 | 9/1986 | Lauks | 204/416 |
| 4,859,306 | 8/1989 | Siddiqi et al. | 204/418 |
| 4,874,499 | 10/1989 | Smith et al. | 204/419 |
| 4,892,640 | 1/1990 | Wolfbeis et al. | 204/416 |
| 5,320,735 | 6/1994 | Kato et al. | 204/419 |

FOREIGN PATENT DOCUMENTS

| | | |
|---|---|---|
| 57-073661 | 5/1982 | Japan . |
| 58-151396 | 9/1983 | Japan . |
| 58-168951 | 10/1983 | Japan . |
| 3021857 | 1/1991 | Japan . |
| 4050648 | 2/1992 | Japan . |

OTHER PUBLICATIONS

Patent Abstracts of Japan, vol. 8, No. 102 (C–222), May 12, 1984, JP-A-59019595 of Feb. 1, 1984.
Patent Abstracts of Japan, vol. 14, No. 462 (P-1113), Oct. 5, 1990, JP-A-2183151 of Jul. 17, 1990.
W. Olthius et al, "Preparation of Iridium Oxide and its Application in Sensor–Actuator Systems", Sensors and Actuators B, 4, (1991) month unavailable, pp. 151–156.
Kinoshita et al, "Talanta", vol. 33, No. 2, pp. 125–134, (1986) month unavailable.
Fog, "Sensors and Actuators", vol. 5, (1984) month unavailable, pp. 137–146.
Grubb et al, "Anal. Chem.", (1980) month unavailable, vol. 52, pp. 270–273.
Handbook of Chemistry and Physics, 1974–1975, month unavailable, 55th ed.

*Primary Examiner*—T. Tung
*Attorney, Agent, or Firm*—Spencer & Frank

[57] ABSTRACT

A member has a solid carrier and a thin oxide layer which is arranged thereon and consists of iridium oxide and/or possibly at least one oxide of at least one other metal belonging to the fifth or sixth period and to one of the subgroups 5b, 6b, 7b and 8 of the Periodic Table of chemical elements and/or zirconium oxide. The oxide layer is monocrystalline and therefore very stable. The member can serve, for example, for the formation of at least one electrode which serves as a proton donor and/or proton acceptor and/or for the measurement and/or change of the pH value and/or for a coulometric measurement or for holding biologically active molecules and at the same time as an electrode and/or optical sensor.

20 Claims, 3 Drawing Sheets 5,507,936

MEMBER FOR THE FORMATION OF AT LEAST ONE ELECTRODE AND/OR ONE SENSOR

This application is a continuation of application Ser. No. 08/073,444, filed Jun. 8, 1993, now abandoned.

BACKGROUND OF THE INVENTION

1. Field of the Invention

The invention relates to a member for the formation of at least one electrode and/or one sensor, having a carrier and a metal oxide layer which is present thereon and consists of at least one oxide of at least one metal belonging to the fifth or sixth period or to one of the subgroups 5b, 6b, 7b or 8 of the Periodic Table of chemical elements and/or of zirconium.

The member may be provided, for example, to form, in contact with an electrically conducting liquid—i.e. an electrolyte—an electrode which acts as a proton donor and/or proton acceptor. The member can be used, for example, for the measurement of the pH value. As will be explained, the member may, however, instead or in addition form or have an electrode and/or sensor for other purposes.

2. Description of the Prior Art

The unexamined Japanese Patent Application 4-050 648 discloses a biochemical sensor having a sapphire lamella which carries a p-doped silicon film. The silicon film is covered with an insulating film on its side facing away from the sapphire lamella. Light emitting diodes by means of which a region of the silicon film can be activated by illumination are also present. This sensor thus has no layer consisting of one of the metal oxides stated further above and has the disadvantage that its silicon film has to be illuminated for the measurement by means of the light emitting diodes.

The unexamined Japanese Patent Application 58-151 396 discloses that an oxide of bismuth and of one of the elements silicon, germanium, gallium or titanium, which oxide has the structure of a gamma-bismuth single crystal, can be heated in order to increase the electrical resistance and then used for the formation of an electro-optical sensor. However, the oxide contains none of the above-mentioned metal oxides present in the member according to the invention.

U.S. Pat. No. 3,726,777 describes a member which has an iridium oxide layer and is used as an electrode for the measurement of the pH value of blood and other liquids. According to this publication, an iridium wire is preferably dipped into a potassium hydroxide solution or sodium hydroxide solution and then heated to about 800° C. in an oxygen environment for the preparation of the oxide layer.

The publication "Preparation of Iridium Oxide and its Application in Sensor-Actuator Systems", W. Olthuis, J. C. van Kerkhof, P. Bergveld, M. Bos, W. E. van der Linden, Sensors and Actuators B, 4, 1991, pages 151–156, Elsevier Sequoia, discloses a member which is provided with an iridium oxide layer and is used as an electrode for donating and accepting hydrogen ions and for coulometric titration. According to the publication, for the production of an electrode, a carrier having a silicon lamella and an iridium film arranged thereon is first produced. This is then oxidized electrochemically in a liquid containing sulfuric acid.

The publication by Olthuis et al. states that the immersion of electrodes in electrolytes for a total period of 120 hours causes a reduction in the proton exchange rate by about 18%, and that two successively performed concentration measurements of hydroxyl ions and hydrogen ions at constant concentrations give deviations of the measured values which are within 2% and 1%, respectively. According to our own investigations of electrodes which were produced by methods of the type described in the cited U.S. Pat. No. 3,726,777 or the cited publication by Olthuis et al., such electrodes do in fact have the disadvantage that their proton acceptance rates and proton donation rates and sensitivities of measurement vary considerably in the course of time. Such changes in the properties of the known electrodes as a function of time can present problems not only in measurements of the pH value but also in other applications of an electrode where the electrode serves as a sensor—i.e. as a measuring element—and/or as a control element and/or as an excitation element.

According to U.S. Pat. No. 3,726,777, the iridium oxide layers known from this publication have a bluish black color. According to our own studies and investigations, the production of oxide layers by methods of the type described in the cited publication by Olthuis et al. also leads to dark, substantially opaque oxide layers. Members having iridium oxide layers of the types known from the cited publications would therefore also be unsuitable as a measuring element for optical methods of measurement in which the oxide layer must be transparent to light.

SUMMARY OF THE INVENTION

It is therefore the object of the invention to provide a member which has at least one metal oxide layer, is suitable for the formation of at least one electrode serving as a measurement and/or control and/or proton exchange and/or excitation element and/or one sensor and eliminates the disadvantages of the known members of this type. When a member is used as a measurement and/or control and/or excitation element, it is desirable in particular that important properties of said element remain stable so that the member permits readily reproducible and accurate measurement, control and/or excitation processes.

The structures of the iridium oxide layers disclosed in U.S. Pat. No. 3,726,777 and in the publication cited by W. Olthuis et al. are not described in detail in these publications. However, our own studies and investigations have shown that the iridium oxide layers produced by the known processes are amorphous and polycrystalline and therefore consist of a large number of very small crystallites, for example crystallites having sizes of less than 0.01 mm. It was further recognised that the stated fluctuations in the proton exchange rates and sensitivities of measurement are due to the amorphous and polycrystalline structures of the oxide layer, because such structures change considerably in the course of time. In an amorphous and polycrystalline oxide layer, gaps may be present and/or may form in particular between the different crystallites and change their size. When an oxide layer having gaps comes into contact with an electrolytic liquid, the latter can penetrate into the gaps and thus form paths for the electric current which pass partially or even completely through the oxide layer and electrically short-circuit said layer. Furthermore, the interfaces between the individual crystallites—especially when gaps are present—can cause refraction, reflection and scattering of light and hence the dark color and opacity of the oxide layer.

The object is therefore achieved, according to the invention, by a member for the formation of at least one electrode and/or one sensor, having a carrier and at least one oxide layer which is arranged thereon, has a free surface region and consists of at least one metal oxide of at least one metal belonging to the fifth or sixth period and to one of the subgroups 5b, 6b, 7b or 8 of the Periodic Table of chemical elements and/or zirconium, wherein at least that part of the or each oxide layer which forms the stated, free surface region of said layer is monocrystalline.

The invention furthermore relates to a means for the coulometric investigation of a liquid, having a member which has a carrier and at least one oxide layer which is arranged thereon, has a free surface region and consists of at least one metal oxide of at least one metal belonging to the fifth or sixth period and to one of the subgroups 5b, 6b, 7b or 8 of The Periodic Table of chemical elements and/or zirconium, wherein at least that part of the or each oxide layer which forms the stated, free surface region of the said layer is monocrystalline, wherein four electrodes which can be brought into contact with the liquid are arranged on the carrier, one of which electrodes serves as a pH measurement electrode, one as a control electrode for controlling the pH value of the liquid by exchanging protons with the liquid, one as a reference electrode for the pH measurement and one as a counter-electrode to the control electrode, the control electrode having a monocrystalline oxide layer comprising at least one oxide of one of the stated metals, and wherein an electronic measuring apparatus electrically connected to the four electrodes is present and is designed to determine the pH value of the liquid on the basis of an electric potential difference between the pH measurement electrode and the reference electrode and to generate an electric current flowing between the control electrode and the counter-electrode through the liquid and to regulate said current so that the measured pH value is equal to a setpoint value.

Advantageous embodiments of the member and of the means are described in the dependent claims.

The or each oxide layer of the member according to the invention has a free surface region, i.e. a surface region which is directly adjacent to a free space and is not covered by a solid material. At least that part of the oxide layer which forms this free surface region, and preferably the entire oxide layer, is monocrystalline and thus has a cohesive, monocrystalline crystal lattice.

The free surface region of the oxide layer may, for example, have a polygonal—for example quadrilateral—or circular contour or may be annular or C-shaped. Depending on the intended use, the size of the free surface region of the oxide layer may be, for example, at least 0.1 mm$^2$ to, for example, about 1000 mm$^2$, and for many purposes in the range from 0.5 mm$^2$ to 100 mm$^2$. An amorphous and polycrystalline oxide layer of the previously known type not according to the invention would contain a very large number of crystallites and gaps with such surface sizes.

The oxide layer may have a flat or so-called ideal surface which is formed by a crystallographic lattice plane on which all surface atoms are completely regularly arranged at sites whose distribution corresponds to the periodic arrangement of the atoms in the interior of a crystal. The actual surface may, however, differ from this ideal surface. For example, the uppermost layer or a group of layers of the atoms may be displaced as a whole and uniformly toward the inner atoms, in which case the surface can still be exactly flat. Furthermore, the atoms of the uppermost layer can be displaced individually and periodically, so that a so-called superstructure is formed. In addition, the periodicity at the surface and in the interior of the oxide layer can be disturbed by irregularly distributed point defects of various types. For example, the atoms may be absent at certain lattice sites and/or slightly displaced and/or interchanged. Moreover, the surface may form at least one step.

It should be noted that the deviations of the oxide layer from the ideal structure and surface of the oxide layer, which deviations are described above, can of course also occur in combination. However, the oxide layer which should still be cohesive, monocrystalline and in general regular and should not consist of a large number of crystallites delimited with respect to one another by interfaces and having differently oriented crystallographic axes.

According to the invention, the or each oxide layer should consist of at least one oxide of at least one metal belonging to the fifth or sixth period and to subgroups 5b or 6b or 7b or 8 of the Periodic Table of chemical elements and/or of zirconium—i.e. of at least one transition metal oxide. The oxide layer preferably consists of an oxide or of oxides of only a single metal from among the stated metals.

If the oxide layer has an oxide of a metal which is oxidizable in different oxidation states, preferably at least that part of the oxide layer which forms the surface of the oxide layer and is adjacent to a free space should consist of the oxide of the highest possible oxidation state. This protects the oxide layer from further oxidation and hence contributes to the chemical stability of the oxide layer.

In a particularly advantageous embodiment of the member, the oxide layer consists of iridium oxide. According to the above data, preferably at least that part of the oxide layer which forms the free surface region of said layer consists of the oxide of the highest oxidation state, i.e. of $IrO_2$.

The oxide layer can, however, also consist of palladium oxide.

Depending on the intended use of the member, it may also be advantageous to form the oxide layer from at least one oxide of one or possibly more of the metals niobium, ruthenium, tantalum, tungsten, osmium, platinum and zirconium.

The oxide layer which, according to the invention, is monocrystalline at least in the free surface region has a stable structure. Furthermore, it has no internal interfaces, in contrast to a polycrystalline oxide layer. This ensures that the oxide layer is compact and completely free from gaps and micro-gaps and, when properly used, also remains free from gaps. If, during its use, the oxide layer comes into contact with a liquid, the latter therefore cannot penetrate into the oxide layer. Since the monocrystalline oxide layer has no internal interfaces and is free from gaps, any optical measurement cannot of course be disturbed by gaps. All these properties ensure that the member having a monocrystalline oxide layer exhibits stable and readily reproducible behavior in the applications described in detail, both in the short term and in the long term.

In an advantageous embodiment of the member according to the invention, its carrier has a carrier part comprising electrically insulating material which is heat-resistant and solid at least to a temperature of 600° C. and preferably at least to a temperature of 800° C. The carrier part can, for example, be formed by a lamella which consists of a crystalline material, such as alumina, namely a piece of a synthetic, transparent, colorless sapphire. The member may furthermore have a metallic support which is arranged on the surface region of the insulating lamella and on which the oxide layer is applied and which consists, for example, of the metal or possibly the metals whose oxide forms the oxide layer or whose oxides form the oxide layer. The oxide layer may then also have, between a layer-like section facing away from the support and consisting of an oxide of the highest oxidation state and the support, a transition section which is adjacent to said support and consists of an oxide of lower oxidation state. It should be noted here that the crystal lattice in the region of such a transition section can also differ from the ideal structure of the single crystal.

if the oxide layer consists of iridium oxide, the support, which is preferably present, can consist of iridium. In this case, the oxide layer may also have a region which consists of $Ir_2O_3$ between a region present am its surface and consisting of $IrO_2$ and the support consisting of iridium.

In an advantageous embodiment of the member according to the invention, a covering is present which, in a plan view of the oxide layer, completely encloses the free surface region of the oxide layer, which region is used for electrical measurement and/or control and/or excitation, and covers the edge region of the oxide layer along the entire edge of said layer. If the member has an electrically insulating carrier part and, between this and the oxide layer, a metallic support, the covering preferably also covers the entire edge of the support. The covering should consist of a material which differs from the oxide layer and—depending on the intended use of the member—can, for example, be liquid-tight and/or opaque and/or electrically insulating. The covering may consist, for example, of pure, undoped silicon or of silica. As already explained, the internal structure and the surface of the oxide layer may differ locally from the ideal structure and from the ideal surface of a single crystal. Since such deviations from the ideal internal structure and the ideal surface occur particularly frequently at the edge of the oxide layer, a covering of the stated type has the advantage that any deviations from the ideal structure and surface which are present in the edge region of the oxide layer are ineffective during the use of the member. In addition, the covering can electrically insulate the edge of any metallic support from the space adjacent to the oxide layer.

The formation and dimensions of the oxide layer and its arrangement on a carrier can be such that it is more or less electrically conducting or semiconducting. As already mentioned, the member provided with the oxide layer can then form at least one electrode. When the member is used as an electrode, the oxide layer can, for example, be brought into contact with an electrically conducting liquid—i.e. an electrolyte. If an electric current is passed through the oxide layer and the electrolyte, the oxide layer can serve as a proton donor and/or proton acceptor. An oxide layer consisting of iridium oxide is particularly advantageous for this purpose because it requires only a small electric electrode potential—i.e. only a small potential present between the electrode and the liquid—for proton exchange. This is, for example, below the potential at which any chloride ions present in the liquid are oxidized and evolved as chlorine. Furthermore, in the case of an electrode having a layer of iridium oxide, the electrode potential required for proton exchange is also smaller than the potential producing electrolytic decomposition of water. An oxide layer consisting of palladium oxide is also suitable for the formation of an electrode used for proton exchange.

A member according to the invention which forms an electrode, namely a measuring electrode, can be used together with another electrode—i.e. a reference electrode—together with electric and/or electronic switching means in order to measure electroanalytically, namely, for example, potentiometrically and/or coulometrically and/or polarographically, the pH value and/or the concentration or activity of any ion and/or the buffer capacity of a liquid consisting of an electrolyte. The reference electrode can consist, for example, at least partly of calomel or silver chloride. It may even be possible for the reference electrode likewise to consist of a member according to the invention and to have an oxide layer which can be brought into contact with the liquid for the measurement. The measurements can be carried out, for example, in blood or in the lymph or in fluid—i.e. in the cerebrospinal fluid—inside or outside a human or animal body. Furthermore, it is also possible to carry out measurements in blood plasma or in urine or in solutions of any type, for example in a lactose and/or glucose solution and/or in a nutrient solution containing a cell culture.

A member according to the invention can furthermore be used as a control element, namely as a working electrode and/or proton exchange electrode and/or titration electrode and/or control electrode in order, in cooperation with another electrode, i.e. a counter-electrode, and with electrical and/or electronic control units, to control, i.e. to influence and to change, the pH value of an electrolytic liquid by exchange, i.e. donation and/or acceptance, of protons.

For example, such a control electrode used for controlling the pH value can then be used together with a counter-electrode and with a pair of electrodes serving for the measurement of the pH value, in order to measure and to control the pH value simultaneously or alternately. The oxide layer of the control electrode used for controlling the pH value may have, for example, a larger surface and/or thickness than the oxide layer of the electrode used for the measurement of the pH value. It is also possible to provide three or only two electrodes for the measurement and control of the pH value. Furthermore, the different electrodes can then be connected to electronic measurement and regulation means in order to adjust the pH value to a predetermined or adjustable setpoint value. If the electrodes are in contact with a liquid in which the pH value is changed as a result of a chemical reaction of a substance and/or as a result of metabolic processes of microorganisms or other cells, the quantity of electric charge consumed during the reaction or during the metabolic processes to keep the pH value constant can also be measured. This is then a measure of the quantity of the stated substance converted in the chemical reaction or of the metabolic processes of the microorganisms or other cells.

A member according to the invention, having an oxide layer of iridium oxide and/or palladium oxide and/or one of the other stated oxides, can also be used for holding biologically active protein and/or peptide molecules on the free surface region, namely for adsorbing said molecules and/or for immobilizing said molecules by means of a chemical bond. The stated molecules may, for example, be taken up directly by the oxide layer and/or physically and/or chemically bound to the oxide layer by means of a binder. Biologically active molecules can then form a molecular layer which is preferably liquid-permeable and, for example, can be brought into contact with a liquid which contains a dissolved and/or dispersed substance which can be chemically changed by the biologically active molecules in such a way that ions—in particular protons or hydroxonium ions or hydroxyl ions—are formed. The member according to the invention can then furthermore serve as an electrode for influencing and/or electroanalytically measuring the quantity of ions by electrically controlled acceptance and/or donation of protons.

In a particularly advantageous embodiment of the member according to the invention, its carrier has an electrically insulating carrier part, for example a one-piece, flat lamella, on which two or more electrodes are arranged. At least one of these electrodes should then have a monocrystalline oxide layer with at least one oxide of one or possibly more of the stated metals and can then serve, for example, as a pH measurement electrode or as a control and/or titration electrode controlling the pH value and/or for titration. Furthermore, for example, at least one of the electrodes present on the lamella or other carrier part can consist of another material and can serve as a reference electrode for the pH measurement and/or as a counter-electrode for controlling the pH value and/or the electroanalytical titration and/or the coulometric measurements. For example, a flat surface of the insulating lamella can be provided with a pH measurement electrode, a reference electrode coordinated therewith, a control and/or proton exchange and/or titration electrode and a counter-electrode coordinated therewith. The carrier part consisting of a lamella, together with at least one other part, can border a free, i.e. empty, space which contains no solid material but is preferably tightly sealed on all sides from the surroundings, said space serving for holding a liquid to be analyzed—in particular a nutrient liquid containing a culture of microorganisms or other cells. The electrodes should be adjacent to this space so that they can be brought into contact with the liquid. The electrodes can be arranged close together and may have relatively small dimensions and, for example, be within a surrounding circle or surrounding square whose diameter or side length is at most 10 mm or even only at most 5 mm. This makes it possible to investigate very small liquid quantities and/or cell cultures very quickly. For example, the amount of acid or acids released by microorganisms or other cells to the nutrient liquid during metabolic processes can be measured coulometrically at a pH value which is kept constant. This amount of acid may then be, for example, a measure of the vitality of the cells and of the effect of drugs or environmental toxins on said cells.

The oxide layer can be rendered light-transmitting or even transparent and more or less clear and colorless by making it thin. The carrier or at least a region thereof carrying the oxide layer can then likewise be made light-transmitting and, for example, even transparent. This makes it possible to carry out, with the aid of light passing through the oxide layer, an optical measurement of biologically active molecules adhering to the oxide layer and/or of living cells in the space adjacent to the oxide layer and/or a microscopic investigation.

The oxide layer of a member according to the invention which forms an electrode or a part of an electrode can furthermore be conductively connected to a nerve strand of a patient or animal directly and/or via an electrically conducting liquid. This electrode can then be used, in cooperation with another electrode, which, for example, likewise has a member according to the invention, and in cooperation with electronic measurement and/or control means, for measuring a parameter—for example the electric voltage and/or the electric current and/or the time behavior—of the nerve signals and/or for generating such signals. The use of an electrode having an oxide layer has the advantage that there is at most a small voltaic polarization and accordingly only a small or practically no contact potential forms between the electrode and the nerve strand. The measurement and/or stimulation of nerve signals can be useful, for example, for diagnostic and/or therapeutic purposes.

The monocrystalline oxide layer can, for example, be produced in a high vacuum by a process based on thin film technology and at the same time applied to the carrier. The oxide layer is preferably applied to a surface formed by a metallic support of the carrier. For the production of an iridium oxide layer, a metallic support consisting of pure iridium can be formed, for example, on an electrically insulating carrier part consisting, for example, of a sapphire lamella in a first vapor deposition process by deposition of the iridium vapor. In a second vapor deposition process directly thereafter, further iridium vapor can be deposited on this metallic support and at the same time oxygen can be passed into the space containing the carrier part. The carrier part can be heated to a temperature of about 600° C. to 800° C., at least during the second vapor deposition process. In the second vapor deposition process, a monocrystalline iridium oxide layer then forms on the metallic support. A monocrystalline metal oxide layer of one of the other stated metals can then also be formed in an analogous manner.

If, in addition to at least one electrode having a metal oxide layer, an electrically insulating carrier part also carries, for example, a reference electrode of silver chloride and/or a counter-electrode of platinum, it is also possible to deposit silver vapor or platinum vapor on the carrier part and subsequently to convert the silver into silver chloride with a chlorine-containing liquid. Similarly, conductor tracks connected electrically to the various electrodes can also be applied to the carrier part by vapor deposition. This permits economical production of a member forming and/or having a plurality of electrodes.

However, it is also possible to apply a metal oxide layer to a metallic support of a carrier, which support has been produced not by vapor deposition but in some other manner. Furthermore, the oxide layer may also be produced by growth of an oxide single crystal and subsequent cutting and/or grinding. The disk formed can then be fastened to the carrier.

In an advantageous embodiment of the member according to the invention, the thickness of the oxide layer is at least 50 nm and at most 1 mm. If the oxide layer is produced by thin film technology, its thickness may be, for example, up to 1000 nm. In the case of a member intended for measuring the pH value or the buffer capacity, it is advantageous to make the oxide layer only about 100 nm to 300 nm thick. Such a relatively small thickness helps to permit rapid measurements. If the member is used for changing the pH value, it is advantageous to make the oxide layer thicker so that it can donate and/or accept sufficient amounts of protons. The oxide layer can then have, for example, a thickness of at least 300 nm to perhaps about 600 nm or more. For optical measurements, it is advantageous to make the oxide layer at most about 300 nm thick, so that it absorbs as little light as possible.

BRIEF DESCRIPTION OF THE DRAWINGS

The subject of the invention will now be explained with reference to embodiments described in the drawings. In the drawings.

Regarding FIGS. 1 to 3, 6 and 7 to 9, it should also be noted that these are schematic and have not been drawn to scale.

DESCRIPTION OF THE PREFERRED EMBODIMENTS

Figure 1:
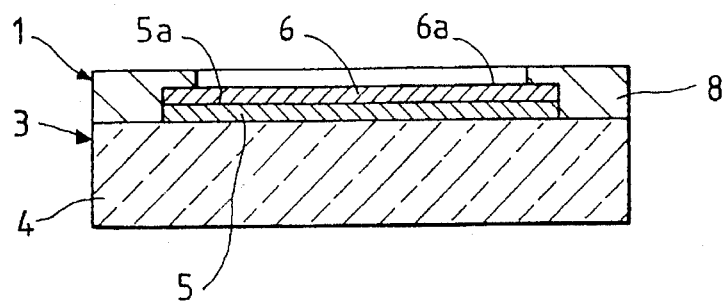
FIG. 1 shows a section through a member which serves as an electrode and has an oxide layer.
Figure 2:
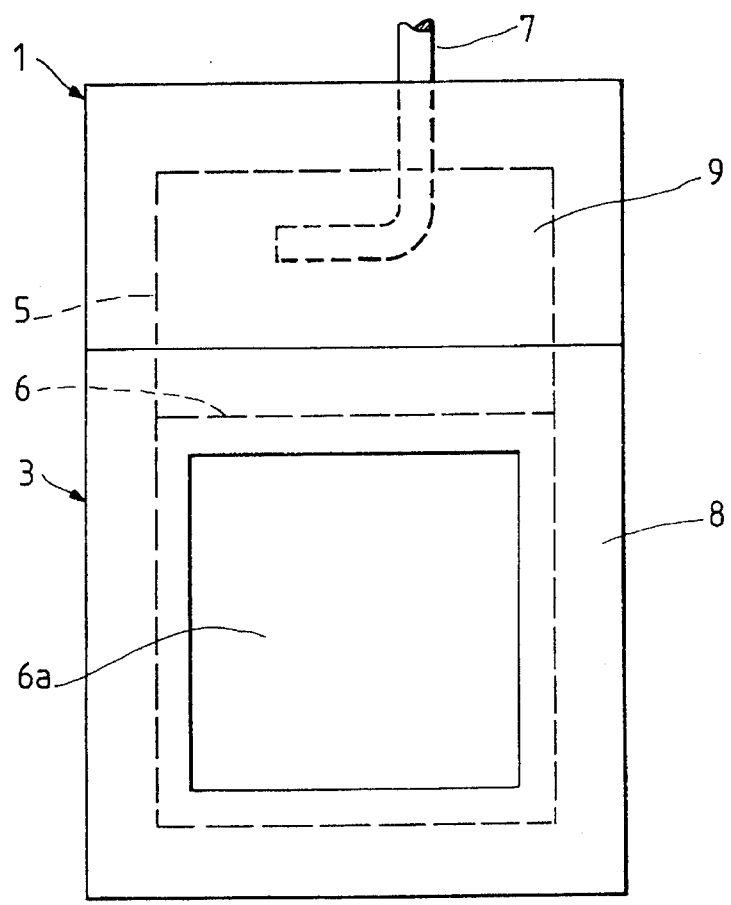
FIG. 2 shows a plan view of the member.

The member 1 shown in FIGS. 1 and 2 has a carrier 3. This has a lamella 4, which forms an electrically insulating carrier part and consists of a disk-shaped crystal fragment of alumina, namely of a transparent and preferably at least approximately colorless, synthetic sapphire fragment. A metallic support 5 which likewise belongs to the carrier 3 and consists of a layer of iridium is arranged on one flat surface of the lamella 4. In the plan view shown in FIG. 2, the outer dimensions of said support are, for example, slightly smaller than those of the lamella 4, so that the latter has an edge region surrounding the support 5 in the stated plan view on all sides. The support 5 has, for example, a slightly elongated, for example quadrilateral contour and is provided on its surface 5a facing away from the lamella 4, with a monocrystalline oxide layer 6 consisting of iridium oxide and firmly and permanently connected to said support. That part of the oxide layers 6 which forms its surface facing away from the support 5 consists of $IrO_2$, as already mentioned in the introduction. On the other hand, that part of the oxide layer 6 which borders the support 5 may—as also already mentioned in the introduction—be less highly oxidized and consist of $Ir_2O_3$. In FIG. 2, the oxide layer 6 is shown with a quadrilateral contour but could also be circular or have some other shape. The quadrilateral edge of the oxide layer 6 is partly flush with that of the support 5. However, the oxide layer 6 covers only a part of the support 5. An electrical conductor 7 is fastened, for example soldered, to that part of the support 5 which is not covered by the oxide layer 6. An electrically insulating covering 8 which consists, for example, of pure undoped silicon applied by vapor deposition encloses the oxide layer 6 in the plan view shown in FIG. 2 and covers an edge region of the oxide layer along the entire edge thereof, sealing it liquid-tight from the space adjacent to the member 1. The covering 8 also covers at least that part of the edge of the support 5 which is flush with the edge of the oxide layer, sealing it liquid-tight from the space adjacent to the member 1. The covering 8 defines a window in which the oxide layer 6 has a free surface region 6a which is directly adjacent to the space surrounding the member 1. That section of the support 6 which is not covered by the oxide layer 6 and is connected to the conductor 7 is covered by an electrical insulation 9 consisting, for example, of an adhesive and/or a synthetic resin, unless it is covered by the covering 8.

Figure 3:
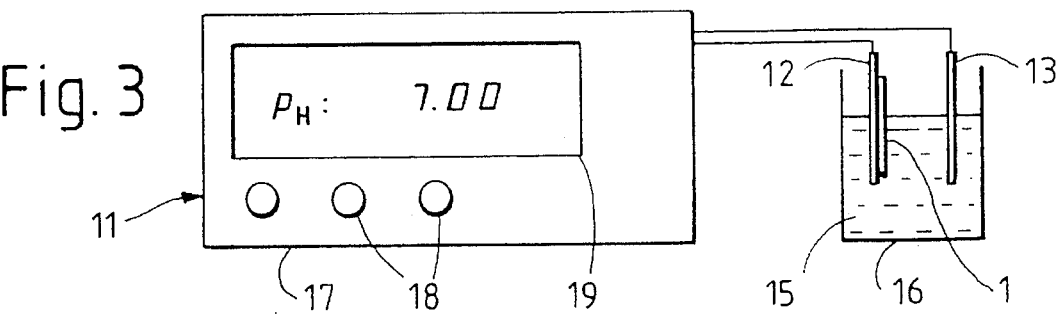
FIG. 3 shows a measuring means having two electrodes.

The measuring means shown in FIG. 3 and designated as a whole by 11 has two measuring elements, namely electrodes 12, 13. The two electrodes 12, 13 project into an electrolytic liquid 15, i.e. a liquid containing at least one dissolved electrolyte. This liquid consists, for example, of blood or blood plasma present in a container 16 of any type.

Electrode 12 serving as a measuring and/or working electrode consists at least partly of the member 1 and also has, for example, a holder which holds the latter. The electrode 12 is arranged so that the oxide layer 6 is in contact with the liquid 15. The electrode 13 serves as a reference electrode and has a section which consists, for example, of calomel and silver chloride and is in contact with the liquid 15.

The two electrodes 12, 13 are connected by electrical conductors to an electronic measuring apparatus 17. This consists of a measuring unit having a housing in which an electric voltage source and electric and electronic switching means are arranged. The measuring unit furthermore has at least one manually operatable control element 18, for example a plurality of such elements, a display apparatus 19 and possibly also a recording apparatus. The measuring means 11 is formed for measuring the pH value of the liquid 15 and, for example, also its buffer capacity, it being possible, for example by means of one of the control elements 18, to select a mode which serves alternately for the measurement of the pH value or of the buffer capacity.

If an electric current is passed through the two electrodes 12, 13 and in particular through the oxide layer 6 of the member 1 belonging to the electrode 12 and through the liquid 15, the iridium oxide can accept or donate protons by means of redox reactions, depending on the direction of the current. These processes can be described in simplified terms by the formula

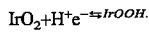

Figure 4:
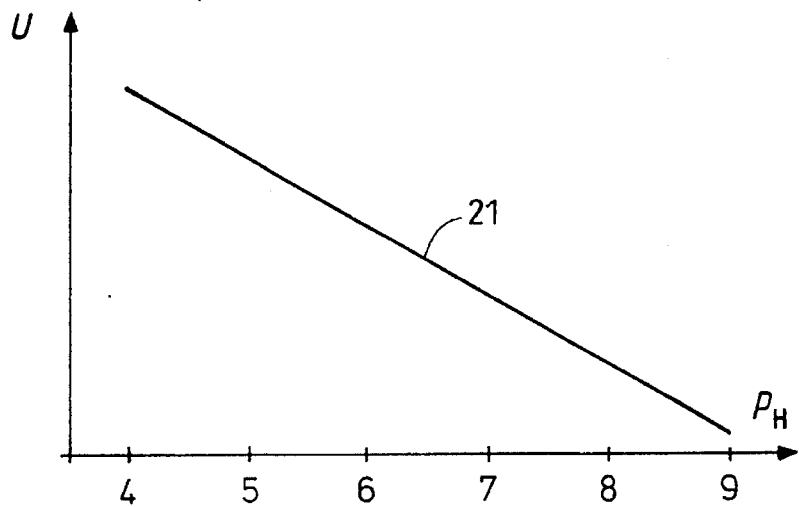
FIG. 4 shows a graph representing the dependence of the electric potential on the pH value.

As disclosed, for example, in U.S. Pat. No. 3,726,777 cited in the introduction, the pH value can be determined by measuring the electric electrode potential. Potentiometric measurements were carried out with the electrodes 12 and 13, which have surfaces of iridium oxide or calomel or silver chloride, which surfaces come into contact with the liquid 15. The results of the measurements are shown in the graph in FIG. 4. In this graph, the pH value is plotted along the abscissa and the electric potential U between the two electrodes is plotted along the ordinate. The relationship between the pH value and the potential U is practically linear at least in a pH range extending approximately from 4 to 9 and is represented by the straight line 21, the pH value increasing with decreasing potential. The measuring unit 17 is formed in order to measure the potential U as a parameter and then to indicate the pH value directly. The measurements have shown that the measured values can be accurately reproduced both in the short term and in the long term.

The electrode 12 having the member 1 can also be used for controlling and/or changing the pH value of the liquid 15 in order to carry out a coulometric measurement, so to speak an electroanalytical titration, and to measure the buffer capacity of the liquid. As in the case of the pH measurement, the electrode 13 can then have, for example, a calomel or silver chloride section or possibly, instead of this, a section consisting of platinum and in contact with the liquid 15.

For carrying out the coulometric measurement and/or electroanalytical titration, the oxide layer 6 can be reduced with the aid of a cathodic current and saturated with protons, for example prior to the measurement or titration, as disclosed in the publication by Olthuis et al., cited in the introduction. During the measurement, a constant electric current is passed through the two electrodes 12 and 13 and the liquid 15, the electrode 12 serving as the anode and its iridium oxide provided beforehand with protons donating protons to the liquid 15.

Figure 5:
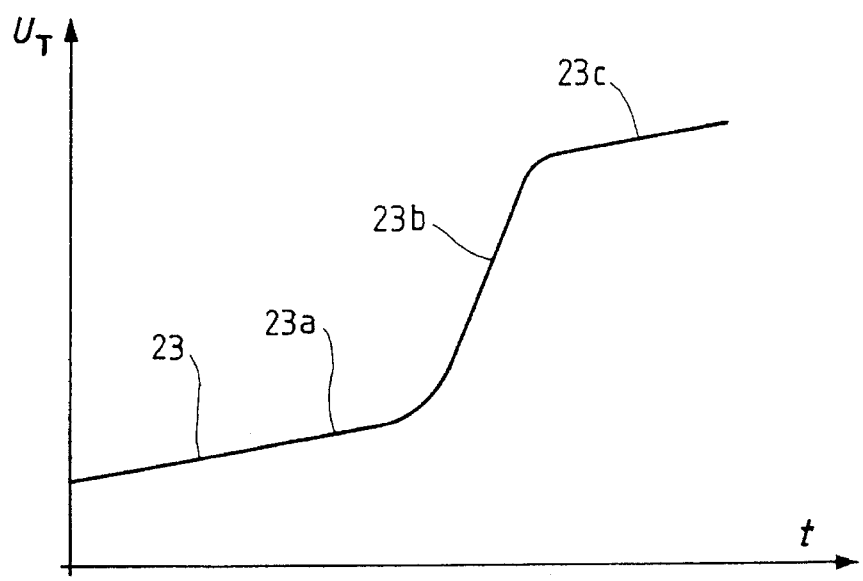
FIG. 5 shows a graph illustrating a coulometric measurement and/or electroanalytical titration.

In the graph in FIG. 5, the time t is plotted along the abscissa and the potential between the two electrodes, designated here by UT, is plotted along the ordinate. The graph also contains a schematic curve 23 which represents the relationship between the time t and the potential UT in the electroanalytical or—more precisely—coulometric measurement and/or titration. If the iridium oxide donates protons in the measurement, the pH value decreases in the course of the time t and the potential $U_T$, which is a measure of this, increases. The curve 23 has three approximately straight curve segments 23a, 23b, 23c connected to one another continuously by curved transitions. The middle, deepest curve segment 23b corresponds to the transition from a relatively basic to a relatively acidic state. The buffer capacity of the liquid 15 is the greater the gentler the steepness of the curve in the pH range considered.

The electronic switching means of the measuring apparatus 17 can be formed, for example, to carry out automatically a measurement or titration of the type illustrated in FIG. 5, in the mode intended for the determination of the buffer capacity, and to determine the potential $U_T$, which is the measure of the pH value, and the value of the differential coefficient $dU_T/dt$, which is a measure of the buffer capacity. The electronic measuring apparatus 17 can furthermore calculate the buffer capacity from the differential coefficient for a predetermined pH range continuously or quasi-continuously and indicate its capacity to the display apparatus.

Figure 6:
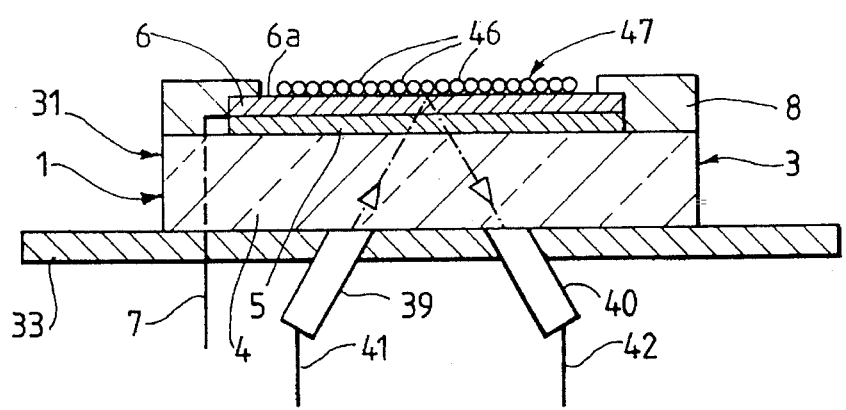
FIG. 6 shows a section through a member for an electroanalytical and optical measurement.

The apparatus shown in FIG. 6 is designated as a whole below as measuring element 31 and has a member 1 which serves as an optical sensor and as an electrode. The member 1 shown in FIG. 6 is in general similar to the member 1 shown in FIG. 1, corresponding parts of the two members being denoted by identical reference symbols. While the support 5 of the member 1 shown in FIG. 1 is formed from iridium, the metallic, electrically conducting support 5 in the member 1 shown in FIG. 6 consists, for example, of a thin layer of indium or tin, which has better light transmittance. The metallic support 5 and the oxide layer 6 of the member 1 belonging to the measuring element 31 are so thin that they are light-transmitting and at least almost clear and transparent, as in the case of the lamella 4 consisting of a slice of a sapphire. The member 1 of the measuring element 31 is fastened to a holder 33 shown schematically and is also provided with and/or connected to a light emitter 39 and a light receiver 40. The light emitter 39 is formed in order to radiate light through the lamella 4, the support 5 and the oxide layer 6. The radiation direction preferably makes a non–90° angle with the free surface region 6a of the oxide layer 6. The light receiver 40 is formed, for example, in order to receive light radiated from the light emitter 39 to the oxide layer 6 and reflected at its surface and convert said light into an electric voltage. The light emitter and the light receiver may have, for example, a light emitting diode or a photodiode and possibly also optical waveguides. Electrical conductors 41 and 42 are connected to the light emitting diode and photodiode.

In order to use the measuring element 31, biologically active molecules 46 are applied to the free surface region 6a of the oxide layer 6 of the member 1 belonging to the measuring element 31. The molecules 46 are bound to the oxide layer by absorption forces and/or immobilized on said layer by chemical bonds, so that they adhere more or less firmly to the oxide layer 6 and form a liquid-permeable molecular layer 47 thereon. The molecules 46 consist of at least one protein and/or peptide and form, for example, an enzyme, such as glucose oxidase. The measuring element 31 can then serve as a part of a measuring means for carrying out measurements on a liquid which contains dissolved glucose. The measuring element 31 can also be arranged, for example in addition to the two electrodes 12, 13 shown in FIG. 3, in a container 16 or in a container corresponding to this. The two electrodes 12, 13 and the conductors 7, 41, 42 of the measuring element 31 can then be connected to a measuring unit designed for investigating the glucose.

If a liquid to be investigated and containing, for example, dissolved glucose is introduced into the container and brought into contact with the measuring element 31, dissolved glucose can reach the molecules 46 and be temporarily bound by them. In carrying out a measurement, light can be radiated through the lamella 4, the support 5 and the oxide layer 6 to the molecular layer 47 by means of the light emitter 39. Depending on the refractive index of the oxide layer 6, on the refractive index of the medium adjacent to it, on the radiation direction and on the wavelength of the light, this light can be completely reflected or partly reflected or partly refracted in the surface region 6a. The refractive index of the molecular layer 47 may be different from the refractive index of the liquid adjacent to it and may furthermore be changed by the glucose temporarily bound to the molecular layer. By suitably establishing the radiation direction and the wavelength of the light, it is therefore possible to enable the glucose bound to the molecular layer 47 to change the ratio of reflected light to refracted light. Consequently, the accumulation of dissolved glucose on the molecular layer 47 can be investigated by an optical or electro-optical measurement.

The molecules 46 consisting of glucose oxidase oxidize the glucose reaching them to gluconic acid. This reduces the pH value of the liquid containing the glucose. The measuring unit connected to the two electrodes 12, 13 and to the measuring element 31 measures the pH value with the aid of the two electrodes 12, 13. The measuring unit furthermore generates an electric current flowing through the liquid between the electrode 13 and the electrode formed by the measuring element 31, and controls the direction and magnitude of said current in such a way that the measuring element 31 regulates the pH value to a predetermined setpoint value by accepting and/or, if necessary, donating protons. The measuring unit is furthermore designed in order to measure the total quantity of electric charge required during the measurement for keeping the pH value constant. This quantity of charge is then a measure of the amount of glucose originally present in the liquid and oxidized to gluconic acid.

It should be noted that a measuring element of the type of measuring element 31 can be used not only for the investigation of glucose-containing liquids but also for a large number of other investigations in which biologically active molecules of at least one protein and/or peptide, held on an oxide layer, can act on a substance which is to be investigated and which is dissolved and/or dispersed in a liquid. For example, it is also possible to apply antibody or antigen molecules to an oxide layer and then to carry out immunological investigations.

Figure 7:
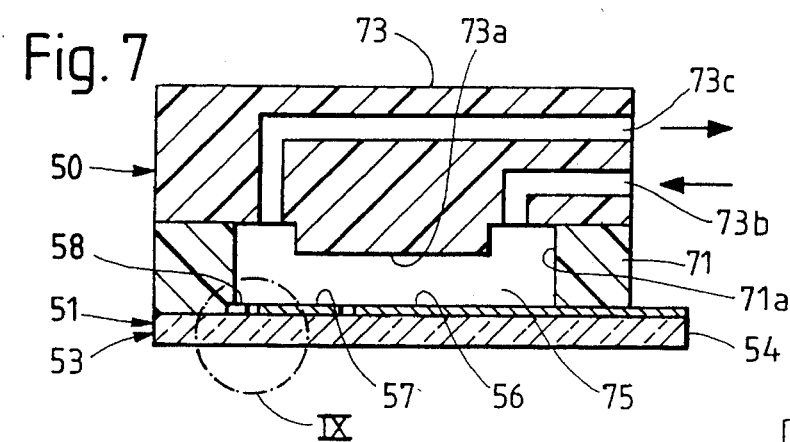
FIG. 7 shows a section through a sensor having a carrier provided with a group of electrodes and having a space which serves for holding a liquid.

A measuring means for coulometric measurements has an apparatus which is shown in FIG. 7 and which forms the sensor 50. This has a member 51 with a carrier 53. The carrier has a carrier part which is formed by an electrical insulating, quadrilateral lamella 54 consisting of a sapphire disk. The lamella 54 is provided, on its flat surface facing upward in FIG. 7, with four electrodes shown in FIG. 8, namely pH measurement electrode 56, a control and/or proton exchange and/or titration electrode 57, a reference electrode 58 and a counter-electrode 59. Each electrode is electrically connected to a conductor track 56a, 57a or 58a or 59a arranged on the lamella. In the plan view shown in FIG. 8, the measurement electrode 56 has a circular section consisting of a complete circle. The control and/or proton exchange and/or titration electrode 57 encloses the measurement electrode 56 almost entirely, namely with the exception of a gap permitting the passage of the conductor track 56a. The control and/or proton exchange and/or titration electrode is thus approximately C-shaped, forms a circular ring interrupted by the stated gap and has a substantially larger surface than the measurement electrode 56. Each of the two electrodes 58, 59 forms an approximately semicircular arc which is narrow compared with electrode 57, and runs along a section of the outer edge of electrode 57. The four conductor tracks run to a section of the edge of the lamella, which section forms a rectangular side of the lamella 54.

Figure 9:
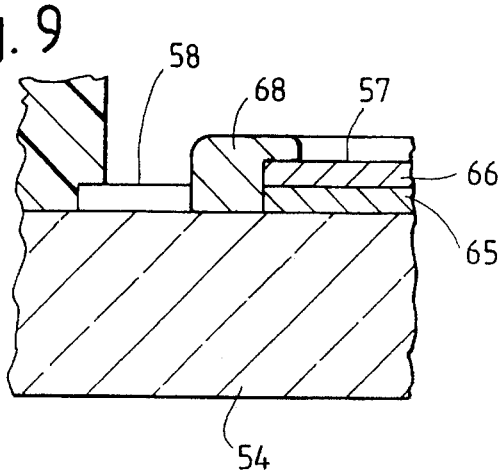
FIG. 9 shows a representation of the section designated by IX in FIG. 7 on a larger scale and with additional parts of the sensor shown in FIG. 7

The measurement electrode 56 and the control and/or proton exchange and/or titration electrode 57, which is partly visible also in FIG. 9, each have a metallic support 65 which is arranged directly on the lamella 54 and consists of a layer of pure iridium applied by vapor deposition and a monocrystalline oxide layer 66 which is present on said support and consists of iridium oxide. The conductor tracks 56a and 57a consist of iridium layers which are cohesive with the support of the electrode 56 or 57. The reference electrode 58 consists of silver chloride, and the conductor track 58a connected to it consists of silver. The counter-electrode 59 and the conductor track 59a connected to it consists of platinum. As already described in the introduction, the electrodes can be produced by vapor deposition and additional measures. The conductor tracks can likewise be formed by vapor deposition.

Between the various electrodes and conductor tracks are gaps which separate these from one another. The edges of the supports 65 forming the electrodes 56, 57 and oxide layers 66 are furthermore covered in a liquid-tight manner by an electrically insulating covering 68 which is visible in FIG. 9 at the outer edge of the electrode 57 and consists, for example, of pure undoped silicon applied by vapor deposition or of silica.

A lamella 71 which has a through hole 71a which is concentric with a group of electrodes 56, 57, 58, 59 and whose diameter is approximately equal to the enveloping circle of the electrode group is arranged on that side of the carrier 53 which is provided with the electrodes.

Also present is a covering part 73 which likewise consists of a lamella, rests on that side of the lamella 71 which faces away from the lamella 54, and has a projection 73a projecting into its hole 71a. The lamellae 54, 71 and the covering part 73 together define a cavity 75 for holding a liquid to be analyzed, which cavity is formed by the free part of the hole 71a and is sealed tightly from the surroundings. The covering part 73 has two passages which enter the cavity 75 between the edge of the projection 73a and the edge of the hole 71a and form an inlet 73b and an outlet 73c for the liquid to be investigated.

The lamella 71 is electrically insulating and consists, for example, of plastic but could also be formed from mineral glass. The covering part 73 consists, for example, of a plastic. The lamella 54 and the covering part 73 are held together preferably by fastening means, for example by a clamping device. The lamella 71 can be permanently connected to the lamella 54 or to the covering part 73 or can be clamped both by the lamella 54 and by the covering part 71, detachably between the latter and the lamella 54. Otherwise, the lamella 71 may rest on the outer edge region of the electrodes 58, 59 according to FIGS. 7 and 9, but should not completely cover said electrodes, so that all electrodes 56, 57, 58, 59 border the cavity 75. The section of the conductor track 56a consisting of iridium, which section is located within the cavity 75 in the plan view, is covered by an insulation against the cavity 75, which insulation consists, for example, of silicon applied by vapor deposition. However, it would also be possible for the electrode 56 to possess, in addition to the circular section present in the center of the other electrodes, also a straight section which is cohesive with said circular section, extends at least to the edge of the cavity 75, is provided with an iridium oxide coating and is not covered by an insulation. It should be noted here that the electrodes applied by vapor deposition and shown in FIGS. 7 and 9 are drawn with greatly exaggerated thicknesses. To ensure that the cavity 75 is tightly sealed from the surroundings when the sensor is assembled, a layer of electrically insulating and elastically deformable sealing and insulating material may also be applied to that region of the lamella 54 which encloses the electrodes 58, 59 and is covered by the lamella 71, and between the conductor tracks and on the latter.

Figure 8:
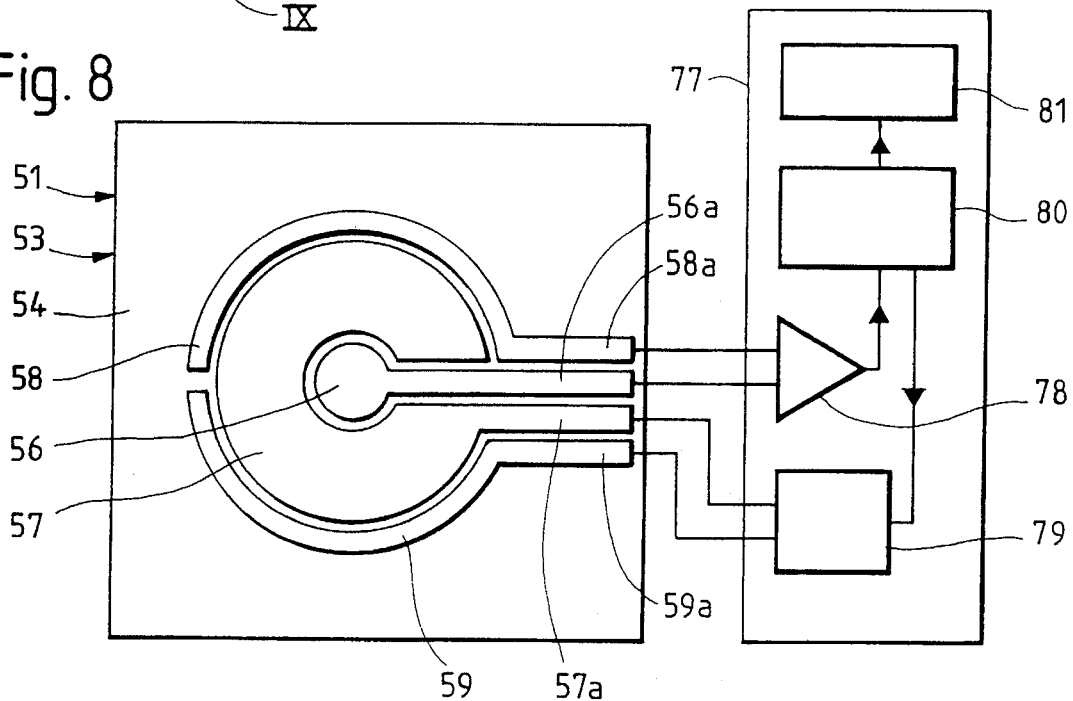
FIG. 8 shows a plan view of the surface of the carrier of the sensor shown in FIG. 7, which surface is provided with electrodes, and a block diagram of an electronic measuring apparatus.

The measuring means having the sensor 50 possesses an electronic measuring apparatus 77, i.e. a measuring unit, the block diagram of which is shown in FIG. 8. The conductor tracks 56a, 57a, 58a, 59a are electrically connected, for example via a plug connector, to the measuring apparatus 77 having electronic switching means. Said measuring apparatus contains a measuring amplifier 78 whose inputs are connected to the pH measurement electrode 56 and to the reference electrode 58. The measuring apparatus 77 furthermore has an electrically controllable current source 79 whose outputs are connected to the control and/or proton exchange and/or titration electrode 57 and to the counter-electrode 59. The measuring apparatus 77 also possesses a measuring and regulation circuit 80 which has, for example, a digital processor. A display and/or recording apparatus 81 is also present. The measuring and regulation circuit 80 is connected to an output of the measuring amplifier 78, to a control connection of the current source 79 and to the display and/or to the recording apparatus 81.

The measuring means having the sensor 50 and the electronic measuring apparatus 77 can be used, for example, for measuring an amount of acid excreted by living cells of a cell culture during metabolic processes. For carrying out a measurement, a suspension sample to be investigated, which consists of a nutrient liquid and cells suspended therein, can be introduced through the inlet 73b into the cavity 75 so that, for example, the suspension completely fills the cavity 75. The amount of acid released by the cells in a certain time can then be measured in the sensor. The measuring and regulation circuit 80 measures the potential difference between the pH measurement electrode 56 and the reference electrode 58, which potential difference is a measure of the pH value of the nutrient liquid. Furthermore, the current source 79 generates an electric direct current flowing through the nutrient liquid between the control and/or proton exchange and/or titration electrode 57. Said current may be uniform or may consist of a sequence of pulses and is directed so that the control and/or proton exchange and/or titration electrode 57 can accept protons from the nutrient liquid. The measuring and regulation circuit 80 regulates the current source 79 in such a way that the proton acceptance by the electrode 57 compensates the amount of protons of the acid released by the cells, and that the instantaneous pH value of the nutrient liquid is equal to a predetermined setpoint value set by means of manually operatable adjusting elements and advantageous for the development of the cells. Furthermore, the measuring and regulation circuit 80 integrates the current flowing for a predetermined, for example manually adjustable, measurement time through the nutrient liquid between the control and/or titration electrode 57 and the counter-electrode, and determines the total quantity of electric charge passed through the nutrient liquid during the measurement time in order to keep the pH value of the nutrient liquid constant. Said quantity is then a measure of the amount of acid released by the cells. The display and/or recording apparatus 81 can then display and/or record, for example, the quantity of charge or a parameter proportional to it and possibly also the pH value.

After a measurement has been carried out, the cavity 75 can be emptied through the outlet 73c, the cavity 75 can be rinsed out and/or, if necessary, the covering part 73 can be temporarily separated from the lamella 54 for cleaning the parts bordering the cavity 75 and a new sample can then be introduced into the cavity 75.

A substance which consists of a drug or of an environmental toxin and whose effect on the cells is to be investigated can also be added to the nutrient liquid before it is introduced into the cavity. In addition, oxygen or another gas can be dissolved in the nutrient liquid, possibly for a measurement. Furthermore, the sensor 50 or at least the suspension present therein during the measurement can be heated or cooled to a temperature which is advantageous for the development of the cells. The sensor 50 can thus, so to speak, form a small bioreactor in which cells can be cultivated and their metabolism investigated.

Figure 10:
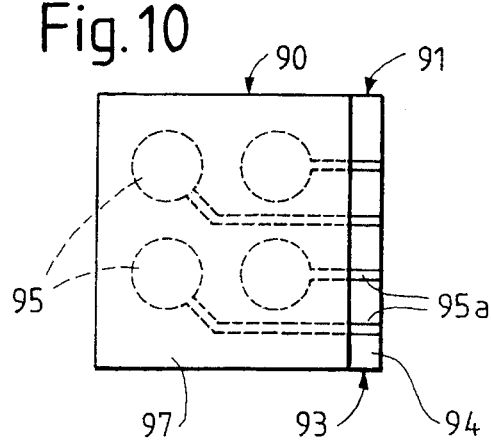
FIG. 10 shows a plan view of an apparatus having a carrier carrying a plurality of groups of electrodes.

The apparatus 90 shown in FIG. 10 forms a multiple sensor and has a member 91 with a carrier 93. This has, as the main component, a lamella 94 which consists of a sapphire disk and on which a plurality, namely, for example, four electrode groups 95 and conductor track groups 95a are mounted. Each electrode group 95 has four electrodes arranged analogously to the electrodes 56, 57, 58, 59. Each conductor track group 95a has four conductor tracks, each of which is connected to an electrode. According to FIG. 10, for example, all conductor tracks can terminate at one and the same quadrilateral side of the quadrilateral lamella 94. The cavity for holding the liquid to be investigated is defined by the lamella 94 together with a covering part 97 corresponding to the covering part 73 and a lamella for each electrode group 95, which lamella is not visible and corresponds to the lamella 71. Otherwise, the covering part 97 can be provided with inlets and outlets which, analogously to the inlet 73b and to the outlet 73c, enter an associated cavity. The apparatus 90, together with a measuring unit, permits a plurality of samples to be investigated simultaneously.

The member according to the invention can furthermore be altered in various aspects. For example, features of different embodiments described can be combined with one another. Furthermore, the lamella 4 or 54 or 94 formed from a sapphire could be replaced by a lamella comprising a metallic or ceramic material or a non-lamellar part. Moreover, the support 5 can be formed from another metallic or nonmetallic material instead of from one of the abovementioned metals iridium, indium or tin. The support 65 can likewise consist of another metal instead of iridium.

In the sensor shown in FIG. 7, the inlet 73b and the outlet 73c can be omitted, and a sample to be analyzed can be introduced by means of a pipette or the like into the cavity temporarily opened by removing the covering part 73. The same also applies to the apparatus 90 which forms a multiple sensor and is shown in FIG. 10. Furthermore, an apparatus which forms a multiple sensor and in which more than 4, for example 6 or 24, electrode groups are present on one and the same one-piece, electrically insulating lamella can also be provided. Moreover, the covering parts 73, 97 and/or possibly the carriers 53, 93 of the apparatuses or sensors shown in FIGS. 7 and 10 can be made transparent so that the cells present in the apparatuses or sensors can also be investigated microscopically and/or by an optical analysis method.

If a member having an oxide layer according to FIG. 6 is to be used as an electrode for holding, i.e. adsorbing and/or immobilizing, biologically active molecules, but need not permit an optical measurement, the support 5 can be formed, for example, from iridium and made opaque, and of course the light emitter 39 and the light receiver 40 can be omitted. If, on the other hand, a member having an oxide layer which serves for adsorbing and/or immobilizing molecules is to permit an optical measurement but need not serve as an electrode, the support 6 may be formed from an electrically insulating material or may be omitted.

What is claimed is:

1. A member for use during chemical analysis of a substance to which the member is exposed, comprising: a carrier; and a metal oxide layer which is arranged on the carrier and which has a plurality of progressively increasing oxidation states as viewed across a thickness of said oxide layer, and a free surface region defining a highest oxidation state, the metal in the layer being selected from the group consisting of metals belonging to one of the fifth and sixth periods and to one of the subgroups 5b, 6b, 7b, and 8 of the Periodic Table of chemical elements and zirconium, wherein at least that part of the oxide layer which forms the free surface region of said layer is monocrystalline.

2. A member as claimed in claim 1, wherein the carrier comprises, a metallic support on which the oxide layer is arranged.

3. A member, as claimed in claim 2, wherein the carrier further comprises a carrier part which consists of alumina and on which a metal layer forming the stated metallic support is arranged.

4. A member for the formation of at least one electrode having a carrier and an oxide layer which is arranged thereon, said oxide layer having a plurality of progressively increasing oxidation states as viewed across a thickness of said oxide layer, and a free surface region defining a highest oxidation state, said oxide layer consisting of a metal oxide of a metal belonging to a group consisting of Ir, Pd, Ru, Ta and Nb, wherein at least that part of said oxide layer which forms said free surface region is monocrystalline.

5. A member as claimed in claim 4, wherein said carrier comprises a metallic support on which said oxide layer is arranged.

6. A member as claimed in claim 5, wherein said oxide layer consists of an oxide of a single metal, and wherein said metallic support also consists of said single metal.

7. A member as claimed in claim 5, wherein said carrier has a carrier part which consists of alumina and on which a metal layer forming said metallic support is arranged.

8. A member as claimed in claim 7, wherein said carrier part consists of a piece of sapphire.

9. A member as claimed in claim 5, further comprising an electrically insulating covering which consists of a material other than said oxide layer and which covers the edge of said metallic support and of said oxide layer, separating them from a space adjacent to said member.

10. A member as claimed in claim 9, wherein said covering consists of silicon or silica.

11. A member as claimed in claim 4, wherein said oxide layer is light-transmitting in said free surface region.

12. A member as claimed in claim 4, wherein one and the same carrier carries at least one electrode having said oxide layer and also at least one additional electrode whose free surface is formed by a material differing from said oxide layer.

13. A member as claimed in claim 12, wherein said material which differs from said oxide layer and serves for forming said at least one additional electrode consists of one substance belonging to a group consisting of silver chloride, calomel and platinum.

14. A member as claimed in claim 4, wherein said carrier has an electrically insulating carrier part and has at least two of said oxide layers which serve as electrodes and are a distance apart.

15. A member for the formation of at least one electrode, serving for at least one of measuring a pH value of a liquid, of measuring an ion concentration of a liquid, of measuring a buffer capacity of a liquid, of detecting electrical nerve signals and of stimulating electrical nerve signals, having a carrier and an oxide layer which is arranged thereon, said oxide layer having a plurality of progressively increasing oxidation states as viewed across a thickness of said oxide layer, and a free surface region defining a highest oxidation state, said oxide layer consisting of a metal oxide of a metal belonging to a group consisting of Ir, Pd, Ru, Ta and Nb, wherein at least that part of said oxide layer which forms said free surface region is monocrystalline.

16. A member having a carrier and an oxide layer which is arranged thereon, said oxide layer having a plurality of progressively increasing oxidation states as viewed across a thickness of said oxide layer, and a free surface region defining a highest oxidation state, for holding biologically active molecules of at least one of a protein and peptide, said oxide layer consisting of a metal oxide of a metal belonging to a group consisting of Ir, Pd, Ru, Ta and Nb, wherein at least that part of said oxide layer which forms said free surface region is monocrystalline.

17. A means for the coulometric investigation of a liquid, having a member which has a carrier and an oxide layer which is arranged thereon, said oxide layer having a plurality of progressively increasing oxidation states as viewed across a thickness of said oxide layer, said oxide layer further having a free surface region defining a highest oxidation state, said oxide layer consisting of a metal oxide of a metal belonging to a group consisting of Ir, Pd, Ru, Ta and Nb, wherein at least that part of said oxide layer which forms said free surface region is monocrystalline, wherein four electrodes are arranged on said carrier which can be brought into contact with said liquid, one of said electrodes serving as a pH measurement electrode, one as a control electrode for controlling the pH value of said liquid by exchanging protons with said liquid, one as a reference electrode for said pH measurement, one as a counter-electrode to said control electrode, said control electrode being composed of the monocrystalline oxide layer, and wherein an electronic measuring apparatus electrically connected to said four electrodes is present and is designed to determine the pH value of said liquid on the basis of an electric potential difference between said pH measurement electrode and said reference electrode and to generate an electric current flowing between said control electrode and said counter-electrode through said liquid and to regulate said current so that the measured pH value is equal to a setpoint value.

18. A means as claimed in claim 17, wherein said pH measurement electrode likewise comprises a monocrystalline oxide layer, wherein said control electrode approximately encloses said pH measurement electrode and wherein said reference electrode and said counter-electrode are arranged outside said control electrode.

19. A means as claimed in claim 17, wherein said carrier, together with at least one part connected thereto, defines a hollow space closed off from the surroundings and adjacent to said four electrodes.

20. A means as claimed in claim 17, wherein said electronic measuring apparatus is formed in order to determine the quantity of electric charge forming said electric current during measurement.

* * * * *